US011285049B2

(12) United States Patent
Ribble et al.

(10) Patent No.: US 11,285,049 B2
(45) Date of Patent: Mar. 29, 2022

(54) TWO LAYER WOUND DRESSINGS INCLUDING REMOVABLE UPPER LAYER

(71) Applicant: Hill-Rom Services, Inc., Batesville, IN (US)

(72) Inventors: David Lance Ribble, Indianapolis, IN (US); Kirsten Emmons, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 350 days.

(21) Appl. No.: 16/381,468

(22) Filed: Apr. 11, 2019

(65) Prior Publication Data

US 2019/0321236 A1 Oct. 24, 2019

Related U.S. Application Data

(60) Provisional application No. 62/659,812, filed on Apr. 19, 2018.

(51) Int. Cl.
*A61F 13/02* (2006.01)
*A61F 13/00* (2006.01)

(52) U.S. Cl.
CPC ...... *A61F 13/0266* (2013.01); *A61F 13/0253* (2013.01); *A61F 13/02* (2013.01); *A61F 13/0226* (2013.01); *A61F 2013/00561* (2013.01)

(58) Field of Classification Search
CPC ................ A61F 13/023; A61F 13/0259; A61F 13/0266; A61F 13/024; A61F 13/0253; A61F 13/0269; A61F 15/008; A61F 2013/00536; A61F 2013/0054; A61F 13/00076; A61F 13/0289; A61F 2013/00889; A61F 17/00; A61F 13/00029; A61F 13/00046; A61F 13/0273; A61F 5/443; A61F 13/0246
See application file for complete search history.

(56) References Cited

U.S. PATENT DOCUMENTS

| 4,399,816 A | 8/1983 | Spangler |
| 4,641,643 A | 2/1987 | Greer |

(Continued)

FOREIGN PATENT DOCUMENTS

| EP | 651985 A2 | 5/1995 |
| EP | 2807994 A2 | 12/2014 |

(Continued)

*Primary Examiner* — Ophelia A Hawthorne
(74) *Attorney, Agent, or Firm* — Dinsmore & Shohl, LLP

(57) ABSTRACT

Wound dressings including a skin contact layer and a cover layer removably adhered to the top surface of the skin contact layer are described. The skin contact layer includes a lower substrate extending around a central aperture and a lower adhesive. The lower substrate includes a top surface and a bottom surface opposite the top surface. The lower adhesive is disposed on the bottom surface of the lower substrate. The cover layer substantially covers the central aperture of the lower substrate, and includes an upper substrate and a backing layer. An upper adhesive is positioned between the top surface of the lower substrate and a bottom surface of the backing layer. In embodiments, the cover layer can be removed and changed while the skin contact layer remains adhered to the skin around a wound.

20 Claims, 4 Drawing Sheets

(56) References Cited

U.S. PATENT DOCUMENTS

| | | | | |
|---|---|---|---|---|
| 4,653,483 | A | * | 3/1987 | Clavin .................. A45D 44/22 |
| | | | | 128/898 |
| 5,415,626 | A | | 5/1995 | Goodman et al. |
| 6,071,267 | A | * | 6/2000 | Zamierowski ...... A61M 1/0058 |
| | | | | 604/289 |
| 8,404,921 | B2 | | 3/2013 | Lee et al. |
| 2006/0029651 | A1 | * | 2/2006 | Brothers ................. C08L 35/04 |
| | | | | 424/445 |
| 2007/0213675 | A1 | * | 9/2007 | Albrecht ............ A61B 17/3421 |
| | | | | 604/264 |
| 2010/0010458 | A1 | * | 1/2010 | Sherman ............... A61F 13/023 |
| | | | | 604/307 |

FOREIGN PATENT DOCUMENTS

| | | |
|---|---|---|
| WO | 9307841 A1 | 4/1993 |
| WO | 0238096 A2 | 5/2002 |
| WO | 2014060625 A1 | 4/2014 |

* cited by examiner

TWO LAYER WOUND DRESSINGS INCLUDING REMOVABLE UPPER LAYER

CROSS-REFERENCE TO RELATED APPLICATIONS

The present application claims priority to U.S. Provisional Patent Application Ser. No. 62/659,812, filed Apr. 19, 2018, and entitled "Two Layer Wound Dressings Including Removable Upper Layer," the entirety of which is incorporated by reference herein.

TECHNICAL FIELD

The present specification generally relates to wound dressings and, more particularly, to two layer wound dressings facilitating removal of the upper layer.

BACKGROUND

Wounds are covered by wound dressings in order to prevent the wounds from becoming infected. Health care providers frequently remove the wound dressings, for example, to evaluate the status of the wound or to change the wound dressing. However, frequent removal of wound dressings can be painful to the patient and may additionally cause damage to the skin, thereby interfering with the healing of the wound.

Accordingly, a need exists for wound dressings that can be removed without causing damage while being adherent enough to provide a barrier to the wound.

SUMMARY

According to some embodiments of the present disclosure, a wound dressing includes a skin contact layer and a cover layer removably adhered to a top surface of the skin contact layer. The skin contact layer includes a lower substrate extending around a central aperture. The lower substrate includes a top surface and a bottom surface opposite the top surface. The skin contact layer also includes a lower adhesive disposed on the bottom surface of the lower substrate to adhere the skin contact layer to the skin of an individual. The cover layer substantially covers the central aperture of the lower substrate, and includes an upper substrate and a backing layer. An upper adhesive is positioned between the top surface of the lower substrate and a bottom surface of the backing layer of the cover layer.

According to some embodiments, of the present disclosure, a wound dressing includes a skin contact layer and a cover layer removably adhered to a top surface of the skin contact layer. The skin contact layer includes a fluid-permeable lower substrate extending around a central aperture. The lower substrate includes a top surface and a bottom surface opposite the top surface. The skin contact layer also includes a lower adhesive disposed on the bottom surface of the lower substrate to adhere the skin contact layer to the skin of an individual. The cover layer substantially covers the central aperture of the lower substrate, and includes an upper substrate and a backing layer. An upper adhesive is positioned between the top surface of the lower substrate and a bottom surface of the backing layer of the cover layer. The upper adhesive has an adhesion factor that is less than an adhesion factor of the lower adhesive.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

Referring now to the illustrative examples in the drawings, wherein like numerals represent the same or similar elements throughout.

DETAILED DESCRIPTION

Figure 1:
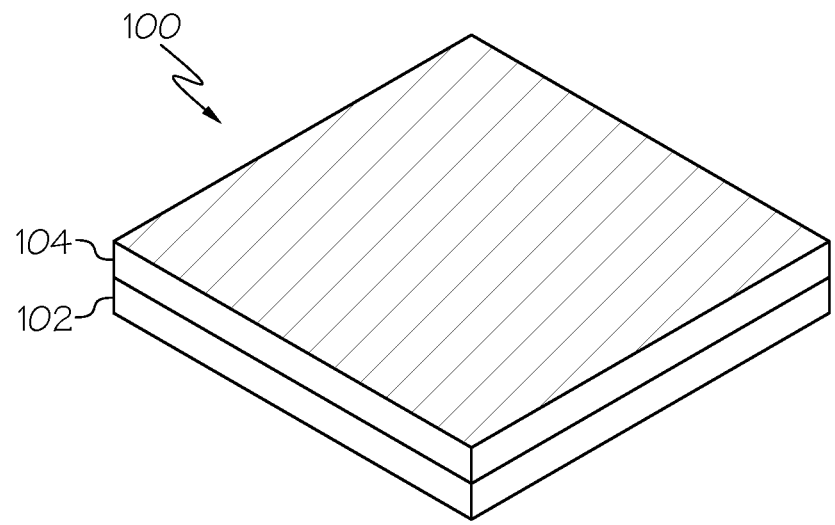
FIG. 1 schematically depicts a wound dressing according to one or more embodiments shown and described herein.

FIG. 1 generally depicts one embodiment of a wound dressing including a skin contact layer and a cover layer. The skin contact layer generally includes a lower substrate and a lower adhesive. The lower substrate extends around a central aperture and includes a top surface and a bottom surface opposite the top surface. The lower adhesive is disposed on the bottom surface of the lower substrate to adhere the skin contact layer to the skin of an individual while the central aperture surrounds a wound of the individual. The cover layer generally includes an upper substrate and a backing layer. An upper adhesive is positioned between the top surface of the lower substrate and a bottom surface of the backing layer to removably adhere the cover layer to the skin contact layer. The cover layer substantially covers the central aperture of the lower substrate, thereby covering the wound. The cover layer can be removed to evaluate the wound or change the dressing while the skin contact layer remains in place so as not to cause damage to the skin or otherwise interfere with the healing of the wound. Various embodiments of wound dressings and the use thereof will be described in more detail herein.

A wound dressing 100 according to various embodiments is depicted in FIG. 1. As shown in FIG. 1, the wound dressing 100 includes a skin contact layer 102 and a cover layer 104 removably adhered to the skin contact layer 102. In practice, the skin contact layer 102 is adhered to the skin of an individual around a wound (i.e., the periwound) and remains in place while the cover layer 104 can be removed and/or changed during healing of the wound.

As shown in FIG. 1, the skin contact layer 102 and the cover layer 104 may have corresponding shapes. Illustratively, the skin contact layer 102 and the cover layer 104 have a roughly square shape that may be appropriate for use in any desired area of an individual's body. However, in other embodiments, the skin contact layer 102 and the cover layer 104 may have any appropriate shape, for example, a circular, rectangular, or triangular shape.

Figure 2:
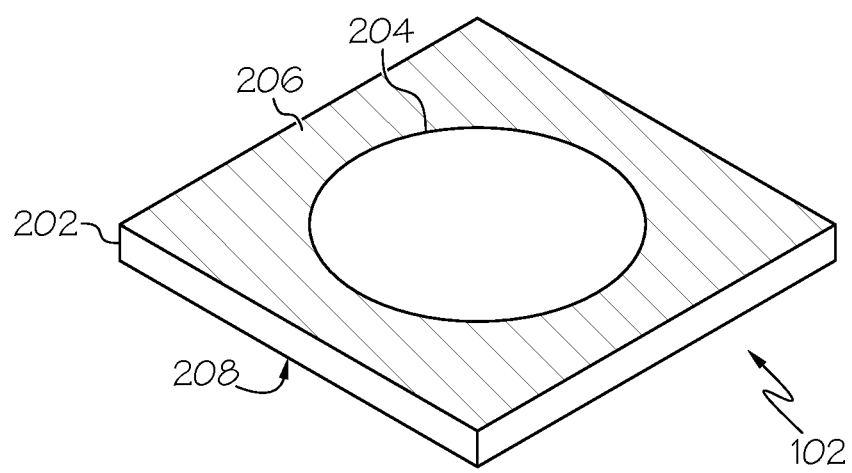
FIG. 2 schematically depicts a skin contact layer of a wound dressing according to one or more embodiments shown and described herein.

FIG. 2 schematically depicts the skin contact layer 102 in greater detail. In particular, the skin contact layer 102 includes a lower substrate 202 extending around a central aperture 204. Although depicted in FIG. 2 as being circular in shape, it is contemplated that the central aperture 204 can have any one of a number of shapes, including square, rectangular, or an irregular shape, provided that the aperture is large enough to surround a wound. The lower substrate 202 includes a top surface 206 and a bottom surface 208 opposite the top surface 206. In various embodiments, the bottom surface 208 contacts the skin of an individual through a lower adhesive to adhere the skin contact layer 102 to the individual while the top surface 206 contacts the cover layer 104.

The lower substrate may be formed from a material that allows the lower substrate to conform to and move with the skin as the individual moves. For example, in various embodiments, the lower substrate 202 can be a flexible, fluid permeable material, such as a fabric or textile, paper, non-woven or quasi-gauze type material. Additionally, the fluid permeability of the material can allow a dissolving solution to pass through the lower substrate 202 and contact the lower adhesive, thereby dissolving the lower adhesive 300 (depicted in FIG. 3) and enabling the removal of the skin contact layer 102 from the skin, as will be discussed in greater detail below.

Figure 3:
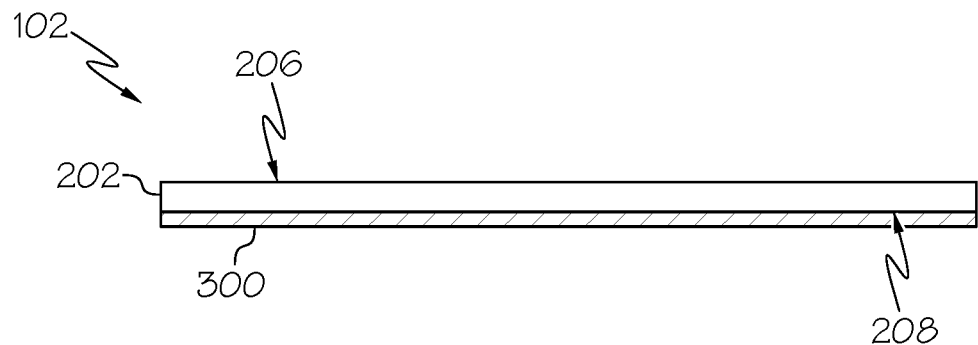
FIG. 3 is a cross-sectional view of a skin contact layer of a wound dressing according to one or more embodiments shown and described herein.

Turning now to FIG. 3, a cross-section of the skin contact layer 102 is shown. As shown in FIG. 3, in various embodiments, the skin contact layer 102 also includes a lower adhesive 300 disposed on the bottom surface 208 of the lower substrate 202. The lower adhesive 300 can be any type of strong adhesive suitable for use on skin. In various embodiments, the lower adhesive 300 is a skin cement, super glue, or other medical grade adhesive. Suitable commercially available adhesives include, by way of example and not limitation, adhesives made available under the tradenames OSTOBOND™ available from Montreal Ostomy, LIQUIBAND™ available from Cardinal Health, DERMABOND™ available from Ethicon, and SKIN AFFIX™ available from Medline Industries, Inc. In various embodiments, the lower adhesive 300 is strong enough to remain adhered to the skin for three, five, seven, or even ten days or more.

In various embodiments, such as the embodiment shown in FIG. 2, the skin contact layer 102 is substantially free of material covering the central aperture 204. In such embodiments, when the skin contact layer 102 is adhered to the skin of an individual, the skin contact layer 102 encircles the wound without touching the wound. However, in other embodiments, such as the embodiment shown in FIG. 4, the skin contact layer 102 further includes a porous, non-adhesive area 400 covering the central aperture 204.

The porous, non-adhesive area 400 can be a mesh or other material that permits extrudate, moisture, and/or therapeutics to pass therethrough. In some embodiments, the porous, non-adhesive area 400 can be formed from a material selected from the group consisting of a non-woven fabric (e.g., containing polyethylene (PE), polyethylene terephthalate (PET), polypropylene (PP), polyamide or polytetrafluoroethylene (PTFE)), a perforated sheet (e.g., containing polyethylene (PE), polyethylene terephthalate (PET), polypropylene (PP), polyamide or polytetrafluoroethylene (PTFE)), a perforated sheet laminated on a non-woven fabric (e.g., containing polyethylene (PE), polyethylene terephthalate (PET), polypropylene (PP), polyamide or polytetrafluoroethylene (PTFE)) a fine net or screen (e.g., containing polyethylene (PE), polyethylene terephthalate (PET), polypropylene (PP), polyamide or polytetrafluoroethylene (PTFE)), a perforated foam or sheet comprising polyurethane, a perforated material based on silicone or a foam with open cells based on polyurethane or silicone or a combination thereof. Accordingly, in some embodiments, the porous, non-adhesive area 400 may be included as part of the skin contact layer 102, such as to provide additional structure to the skin contact layer 102, without impacting the efficacy of the cover layer or otherwise damaging the wound.

Figure 4:
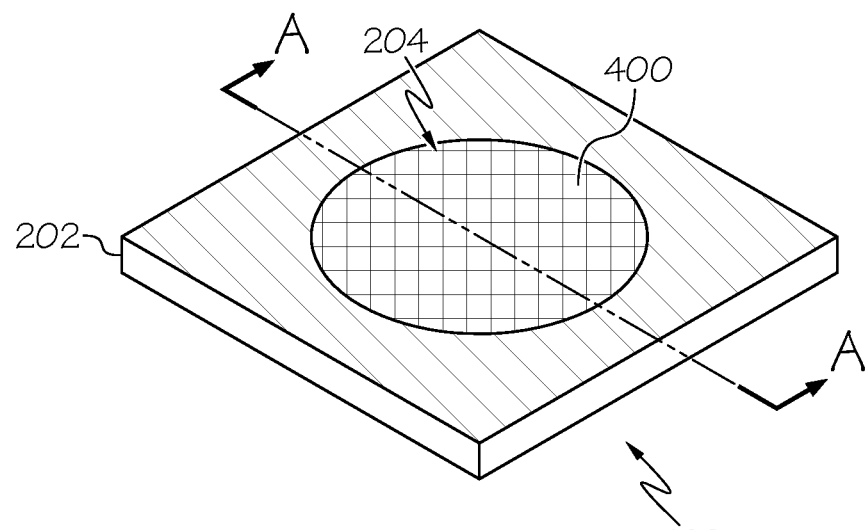
FIG. 4 schematically depicts a skin contact layer having a porous, non-adhesive area covering the central aperture according to one or more embodiments shown and described herein.
Figure 5:
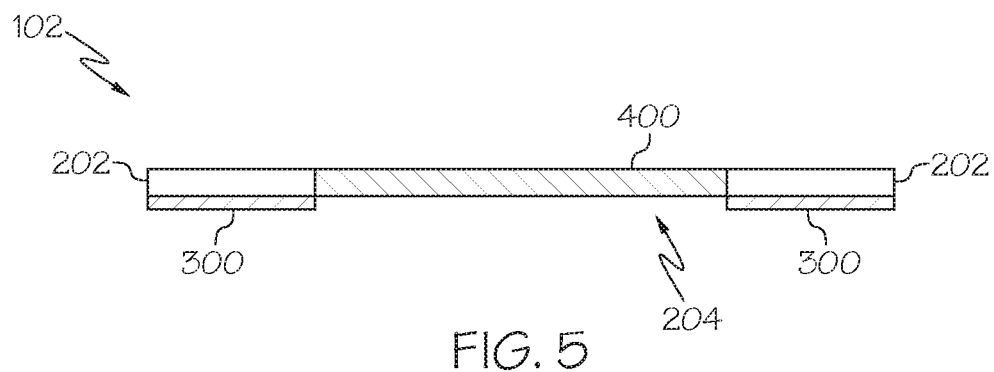
FIG. 5 is a cross-sectional view of the skin contact layer of FIG. 4 along line A-A according to one or more embodiments shown and described herein.

FIG. 5 is a cross-section of the skin contact layer 102 in FIG. 4 along line A-A. As shown in FIG. 5, the lower adhesive 300 disposed on the bottom surface of the lower substrate 202 is not disposed on the porous, non-adhesive area 400. The porous, non-adhesive area 400 may be joined to the lower substrate 202 in any suitable manner, for example, gluing, stitching, stapling, heat sealing, or the like. Additionally, although depicted in FIG. 5 as being joined to the lower substrate 202 along an edge of the porous, non-adhesive area 400, it is contemplated that in some embodiments, the porous, non-adhesive area 400 may at least partially overlap the lower substrate 202, such that a bottom surface of the porous, non-adhesive area 400 is in contact with the top surface of the lower substrate 202.

Moreover, although the porous, non-adhesive area 400 is depicted in FIG. 5 as having a thickness that is substantially the same as the thickness of the lower substrate 202, it is contemplated that, in some embodiments, the porous, non-adhesive area 400 can have a thickness that differs from the thickness of the lower substrate 202. For example, in some embodiments, the porous, non-adhesive area 400 may have a thickness that is less than a thickness of the lower substrate such that at least one of the top surface and the bottom surface of the porous, non-adhesive area 400 is non-planar with respect to at least one of the top surface and the bottom surface, respectively, of the lower substrate 202.

Accordingly, various embodiments of the skin contact layer 102 described herein enable the skin contact layer 102 to be adhered to the skin of an individual in a semi-permanent manner while the central aperture 204 prevents adhesion of the lower substrate 202 to the wound while simultaneously enabling the wound to be exposed upon removal of the cover layer from the skin contact layer 102. Thus, the cover layer can be removed for evaluation of the wound without removal of the skin contact layer 102 from the periwound.

Figure 6:
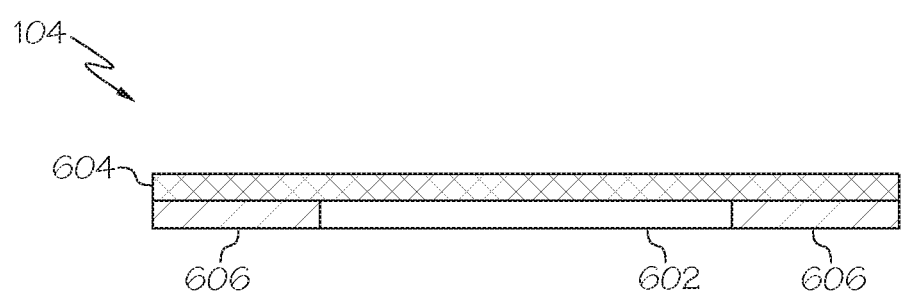
FIG. 6 is a cross-sectional view of the cover layer of a wound dressing according to one or more embodiments shown and described herein.

Turning now to FIG. 6, a cross-section of the cover layer 104 is shown in detail. In various embodiments, the cover layer 104 is constructed of soft, compliant material with layers that apply limited pressure and shear to the individual. According to various embodiments, the cover layer 104 includes an upper substrate 602, a backing layer 604, and an upper adhesive 606. In various embodiments, the upper adhesive 606 is positioned between the bottom surface of the backing layer 604 and the top surface of the lower substrate (not shown in FIG. 6).

In various embodiments, the upper substrate 602 can be in the form of an absorbent layer and/or a moisturizing layer, for example. The absorbent layer transports wound fluid (exudate) away from the wound and absorbs exudate. In some embodiments, the absorbent layer may allow lateral spread of the exudate to maximize absorbency, while in other embodiments, the absorbent layer may limit lateral spread of the exudate. The reduction in lateral spread afforded by a wound dressing may reduce maceration of skin surrounding the wound.

The moisturizing layer provides the wound with moisturizing or other suitable wound treatment (therapeutic) compounds, including but not limited to, biologics, antibiotics, or the like. Accordingly, in various embodiments, the moisturizing layer is a layer impregnated or saturated with an active agent, such as a moisturizer, biologic, antibiotic, or the like. In one embodiment, the moisturizing layer is a hydrogel, alginate, silver ion, foam, hydrocolloid, or mesalt layer. The moisturizing layer can, in various embodiments, release the active agent from the moisturizing layer to be absorbed by the wound. In such embodiments, the cover layer can be replaced when the moisturizing layer has released a substantial portion the active agent. However, in other embodiments, the active agent can be maintained within the moisturizing layer at a location proximate to the wound.

In embodiments, the upper substrate 602 is fibrous and, for example, includes gel forming fibers. In various embodiments, the upper substrate 602 is non-woven. Without being bound by theory, it is believed that fibrous layers are advantageous because they are able to gel block which resists the lateral spread of exudate. In addition, exudate is absorbed rapidly and retained under pressure. Fibers suitable for use include, by way of example and not limitation, hydrophilic fibers which upon the uptake of wound exudate become moist and slippery or gelatinous and thus reduce the tendency for the surrounding fibers to adhere to the wound. In some embodiments, the fibers can be of the type which retain their structural integrity on absorption of exudate, or they can be of the type which lose their fibrous form and become a structure-less gel or a solution on absorption of exudate. Gel forming fibers can be, for example, chemically-modified cellulosic fibers, such as carboxymethylated cellulose fibers.

The upper substrate 602 may, in addition to or as an alternative to the gel forming fibers, also comprise other fibers such as textile fibers which can be natural or synthetic such as cellulosic fibers, for example, viscose rayon, multi-limbed viscose, cotton, or regenerated cellulose or fibers having a higher absorbency than most textiles. Without being bound by theory, the use of a blend of gel forming and cellulosic fibers may reduce shrinkage of the dressing. In particular, the inclusion of the cellulosic fibers may help maintain the shape and structure of the upper substrate 602 while in use.

In still other embodiments, the upper substrate 602 can be an absorbent polymeric substrate, a foam, an alginate, or a hydrocolloid. Absorbent polymeric materials may include, by way of example and not limitation, modified starch, polymerized polyvinyl alcohol, polyethylene oxide, and polyacrylates. Foams suitable for use include flexible, open-cell foams that are at least slightly hydrophilic. Without being bound by theory, the open cells permit transport of fluid and cellular debris into and through the foam. Various cell sizes are contemplated, provided that they are large enough to promote fluid transport through the layer. Suitable foams can include foams made from polyurethane, cellulose, carboxylated butadiene-styrene rubber, polyester foams, hydrophilic epoxy foams or polyacrylate.

Suitable hydrocolloids include, but are not limited to, natural gums such as arabic gum, ghatti gum, karaya gum, tragacanth gum, guar gum, locust bean gum and acacia gum; seaweed extracts such as agar, algin, alginate salts and carrageenan; cereal gums; starches; fermentation or microbial gums such as dextran gum and xanthan gum; pectins; gelatins; casein; and collagens. Modified forms of the hydrocolloids may also be used, including, for example, the oxidized, acetylated, carboxylated, esterified, methylated, aminated, etherated, sulfated, borated and phosphated derivatives of the hydrocolloid absorptive agents. Suitable synthetic gums include polyvinylpyrrolidone, low methoxyl pectin, propyleneglycol alginates, carboxymethyl locust bean gum and carboxymethyl guar gum.

Other materials are contemplated for use as the upper substrate 602, provided they are suitable for medical use. Additionally, it is contemplated that the particular material forming the upper substrate 602 can be selected based on the status of the wound to which the wound dressing 100 is to be applied. For example, an upper substrate 602 formed from a superabsorbent material, calcium alginate, and/or collagen can be utilized when the wound has heavy drainage, while an upper substrate 602 formed from a hydrogel gauze or hydrogel sheet can be utilized when the wound is a dry wound with minimal wound drainage.

In various embodiments, the upper substrate 602 can be in the form of a sheet, although it is contemplated that in some embodiments, the upper substrate 602 can include patterning or other structural features to enhance the absorbency of the upper substrate 602. For example, channels or receptacles can be formed in the upper substrate 602 to direct the exudate away from the periwound and redistribute the exudate through the upper substrate 602.

The backing layer 604 may be of any suitable material known for use in the preparation of wound dressings (e.g. a foam, a non-woven layer or a polyurethane, polyethylene, polyester or polyamide film). In various embodiments, the backing layer 604 is water impermeable and vapor permeable, such as a layer made from a coated woven or non-woven nylon or polyester, a polyurethane film, or the like. In embodiments in which the backing layer 604 is a coated layer, the coating may be, for example, a thermoplastic polyurethane. Without being bound by theory, the use of a water impermeable, vapor permeable material as the backing layer 604 enables the dressing to be worn while the individual bathes or showers without the wound becoming wet. In various embodiments, the backing layer 604 provides a barrier to bacteria (including MRSA), viruses, and other external contaminants, sealing the wound area from external pathogens.

In some embodiments, the cover layer 104 may also include a facing layer (not shown) positioned between the upper substrate 602 and the central aperture 204 of the skin contact layer 102. The facing layer can be formed from a material selected from the group consisting of a non-woven fabric (e.g., containing polyethylene (PE), polyethylene terephthalate (PET), polypropylene (PP), polyamide or polytetrafluoroethylene (PTFE)), a perforated sheet (e.g., containing polyethylene (PE), polyethylene terephthalate (PET), polypropylene (PP), polyamide or polytetrafluoroethylene (PTFE)), a perforated sheet laminated on a non-woven fabric (e.g., containing polyethylene (PE), polyethylene terephthalate (PET), polypropylene (PP), polyamide or polytetrafluoroethylene (PTFE)) a fine net or screen (e.g., containing polyethylene (PE), polyethylene terephthalate (PET), polypropylene (PP), polyamide or polytetrafluoroethylene (PTFE)), a perforated foam or sheet comprising polyurethane, a perforated material based on silicone or a foam with open cells based on polyurethane or silicone or a combination thereof. In embodiments in which a facing layer is included as part of the cover layer 104, the facing layer may reduce sticking between the upper substrate 602 and the wound area. Accordingly, in some embodiments, the facing layer may be coated with a non-sticking material, such as silicone.

In various embodiments, the cover layer 104 can additionally include one or more additional therapeutic layers. The therapeutic layer may include, by way of example and not limitation, moisture-retentive foam, film, hydrogel, hydrocolloid, alginates, biologics, skin substitutes, and combinations thereof. In some embodiments, the cover layer 104 may include components forming a negative pressure wound therapy (NPWT) system. The cover layer 104 may also include, an odor-absorbing layer, such as an activated carbon layer, or the like, in some embodiments. Although it is contemplated that a therapeutic layer can be included as a distinct layer within the cover layer 104, in some embodiments, therapeutic agents, including moisture-retentive foams, films, hydrogels, hydrocolloids, alginates, biologics, and/or skin substitutes can be incorporated into other layers of the cover layer 104, such as the upper substrate 602.

The layers of the cover layer 104, including at least the upper substrate 602 and the backing layer 604, can be connected together using any suitable method. For example, the backing layer 604 may be adhered to the upper substrate 602 using an adhesive, heat sealed, crimped, stitched, or embossed. However, other methods for joining the layers together are contemplated.

As shown in FIG. 6, the cover layer 104 further includes an upper adhesive 606. The upper adhesive 606 can be, for example, an adhesive comprising an acrylate, silicone, synthetic rubber, thermoplastic rubber, or the like. Alternatively or additionally, the upper adhesive 606 can be a blend of one or more hydrocolloids and one or more polyisobutylenes. Hydrocolloids can include, by way of example and not limitation, sodium carboxymethylcellulose, pectin, gelatin, guar gum, locust bean bum, karaya gum, and the like. Although various adhesives are described herein, it is contemplated that other adhesives can be used, depending on the particular embodiment.

In various embodiments, the upper adhesive 606 has an adhesion factor that is less than an adhesion factor of the lower adhesive 300. As used herein, the "adhesion factor" refers to the tensile adhesion strength of the adhesive, measured in accordance with EN 12004. When the upper adhesive 606 has an adhesion factor that is less than the adhesion factor of the lower adhesive 300, a force applied to the cover layer 104, such as when an individual attempts to lift or peel the cover layer 104, will enable the cover layer 104 to be removed from the skin contact layer 102, while the skin contact layer 102 remains adhered to the skin.

Figure 7:
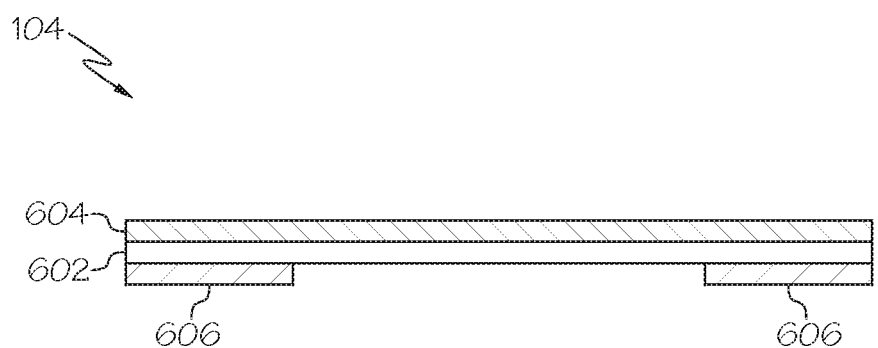
FIG. 7 is a cross-sectional view of an alternative cover layer of a wound dressing according to one or more embodiments shown and described herein.

In the embodiment depicted in FIG. 6, the upper adhesive 606 is disposed on the bottom surface of the backing layer 604. However, it is contemplated that in some embodiments, the upper adhesive 606 may be disposed on the upper substrate 602, as shown in FIG. 7. In other words, in some embodiments, the upper substrate 602 extends between the upper adhesive 606 and the bottom surface of the backing layer 604. In still other embodiments, the upper adhesive 606 can be disposed on the bottom surface of another one of the layers in the cover layer 104, such as a facing layer, or the like. Regardless of the particular layer on which the upper adhesive 606 is disposed, in various embodiments, the upper adhesive 606 does not extend into an area of the cover layer 104 that corresponds to the central aperture 204 of the lower substrate 202. Thus, when the cover layer 104 is adhered to the skin contact layer 102 and substantially covers the central aperture 204 of the lower substrate 202, the upper adhesive 606 does not extend into the central aperture 204 and instead remains between the top surface of the lower substrate 202 and the bottom surface of the backing layer 604. Accordingly, the upper adhesive 606 adheres the cover layer 104 to the skin contact layer 102 without adhering to the skin exposed by the central aperture 204.

In various embodiments, the cover layer 104 may be made from materials that render the wound dressing 100 suitable for use in negative pressure wound therapy (NWPT). Typically in NPWT the wound cavity or surface is filled or covered with a material that allows the transmission of a partial vacuum (i.e., does not completely collapse) to the wound bed when a negative pressure is applied to the wound area, and also allows fluids to pass from the wound bed towards the source of negative pressure. There are two primary approaches to NPWT, gauze or foam types. The gauze type (also referred to as the Chariker-Jeter technique) involves the use of a drain wrapped in gauze topped by a sealed dressing. The foam type involves the use of foam placed over or in the wound. Accordingly, in various embodiments, the cover layer 104 can include gauze or foam, such as in the form of the upper substrate 602.

In embodiments in which the cover layer 104 is suitable for use in NWPT, it is contemplated that the cover layer 104 may include one or more apertures suitable for a tube connected to a vacuum source to be inserted through. Accordingly, when the wound dressing 100 is in place, fluid may be transmitted through the tube to a collection receptacle positioned between the end of the tube and the vacuum source.

When the wound dressing 100 is in use, the wound dressing 100 is adhered to the skin of an individual by placing the lower adhesive 300 into contact with the skin. In various embodiments, the wound dressing 100 is positioned such that the central aperture 204 extends over the wound area and no adhesive (e.g., lower adhesive 300 or upper adhesive 606) is in contact with the wound area. In embodiments, a backing strip or other removable layer may be removed from the wound dressing 100 in order to expose the lower adhesive 300 for contacting it with the skin.

The skin contact layer 102 can remain in contact with the skin through the lower adhesive 300 for an extended period of time (e.g., three, five, seven days or more). When in place, the cover layer 104, and more particularly, the upper substrate 602, can absorb the exudate, such as by capillary action. In embodiments, the upper substrate 602 can wick the exudate away from the wound surface. In embodiments in which the upper substrate 602 includes a therapeutic agent, such as a moisturizer or other type of treatment, the therapeutic agent can be released from the upper substrate 602 and absorbed by the wound.

After a predetermined period of time, the cover layer 104 can be removed from the skin contact layer 102 by lifting the cover layer 104 from the top surface of the skin contact layer 102, which remains in place. The frequency with which the cover layer 104 is removed or replaced can vary depending on the particular embodiment and can, for example, depend on the particular type of wound, treatment protocols, and care standards. In some embodiments, the cover layer 104 is removed when the upper substrate 602 has reached its maximum capacity, such as when the upper substrate 602 is an absorbent layer. In other embodiments, the cover layer 104 is removed when the upper substrate 602 has emptied, such as when the upper substrate 602 is a therapeutic or moisturizing layer.

The cover layer 104 can be, for example, completely removed from the skin contact layer 102 and replaced with a new cover layer 104, or partially or completely removed from the skin contact layer 102 and can be put back in place after the wound is evaluated. In some embodiments, a first cover layer 104, for example a cover layer 104 in the form of a calcium alginate dressing, may be removed after a wound has partially healed, and a second cover layer, such as a cover layer in the form of a hydrogel sheet can be adhered to the skin contact layer 102. Accordingly, various embodiments enable the wound dressing to be removed and replaced as needed during the healing of the wound without damaging the skin, since the skin contact layer 102 remains in place.

In some embodiments, when the wound is healed, the cover layer 104 may be removed from the skin contact layer 102 and an adhesive dissolution solution may be applied to the lower substrate 202. The adhesive dissolution solution can be, for example, saline, alcohol, or a commercially available solution suitable for dissolution of an adhesive, such as the solution available under the tradename DETA-CHOL™ (Ferndale IP, Inc.). As used herein, the phrase "dissolution of an adhesive" includes dissolving the adhesive as well as decreasing the strength of the adhesive to enable the skin contact layer 102 to be removed from the skin. The lower substrate 202 enables the solution to contact and dissolve the lower adhesive 300, enabling removal of the skin contact layer 102 from the skin without damaging the skin. However, in other embodiments, a force may be applied to the skin contact layer 102 to remove the skin contact layer 102 from the skin after the wound is healed, depending on the particular embodiment. Accordingly, the skin contact layer 102 may be removed from the skin only once, despite the ability to regularly replace the dressing over the wound via the cover layer 104.

Many additional embodiments other than those described above are possible and still included in the spirit and scope of the claims defining the embodiments described herein. For example, although various combinations of features of a wound dressing have been shown and described, it is contemplated that these features may be combined in other ways described in detail or illustrated in the accompanying figures.

In a first aspect, the disclosure provides a wound dressing comprising a skin contact layer and a cover layer. The skin contact layer comprises a lower substrate extending around a central aperture. The lower substrate comprises a top surface and a bottom surface opposite the top surface. The skin contact layer also includes a lower adhesive disposed on the bottom surface of the lower substrate. The cover layer is removably adhered to the top surface of the skin contact layer and substantially covers the central aperture of the lower substrate. The cover layer comprises an upper substrate and a backing layer. An upper adhesive is positioned between the top surface of the lower substrate and a bottom surface of the backing layer of the cover layer.

In a second aspect, the disclosure provides the wound dressing of the first aspect, wherein the lower substrate of the skin contact layer is fluid-permeable.

In a third aspect, the disclosure provides the wound dressing of the first or second aspects, wherein the lower adhesive comprises skin cement or super glue.

In a fourth aspect, the disclosure provides the wound dressing of any preceding aspect, wherein the skin contact layer further comprises a porous non-adhesive area covering the central aperture.

In a fifth aspect, the disclosure provides the wound dressing of any one of the first through third aspects, wherein the skin contact layer is substantially free of material covering the central aperture.

In a sixth aspect, the disclosure provides the wound dressing of any preceding aspect, wherein the backing layer is water impermeable and vapor permeable.

In a seventh aspect, the disclosure provides the wound dressing of any preceding aspect, wherein the upper substrate is an absorbent layer.

In an eighth aspect, the disclosure provides the wound dressing of any preceding aspect, wherein the upper substrate is a moisturizing layer.

In a ninth aspect, the disclosure provides the wound dressing of any preceding aspect, wherein the upper adhesive has an adhesion factor less than an adhesion factor of the lower adhesive.

In a tenth aspect, the disclosure provides the wound dressing of any preceding aspect, the cover layer further comprising a moisture-retentive foam, film, hydrogel, hydrocolloid, biologic, alginate, or combination thereof.

In an eleventh aspect, the disclosure provides the wound dressing of any preceding aspect, wherein the upper substrate extends between the upper adhesive and the bottom surface of the backing layer.

According to a twelfth aspect, the disclosure provides a wound dressing comprising a skin contact layer and a cover layer. The skin contact layer comprises a lower substrate extending around a central aperture. The lower substrate comprises a top surface and a bottom surface opposite the top surface. The skin contact layer also comprises a lower adhesive disposed on the bottom surface of the lower substrate. The lower substrate is fluid-permeable. The cover layer is removably adhered to the top surface of the skin contact layer and substantially covers the central aperture of the lower substrate. The cover layer comprises an upper substrate and a backing layer, wherein an upper adhesive is positioned between the top surface of the lower substrate and a bottom surface of the backing layer of the cover layer. The upper adhesive has an adhesion factor less than an adhesion factor of the lower adhesive.

According to a thirteenth aspect, the disclosure provides the wound dressing of the twelfth aspect, wherein the lower adhesive comprises skin cement or super glue.

According to a fourteenth aspect, the disclosure provides the wound dressing of the twelfth or thirteenth aspects, wherein the skin contact layer further comprises a porous non-adhesive area covering the central aperture.

According to a fifteenth aspect, the disclosure provides the wound dressing of the twelfth or thirteenth aspects, wherein the skin contact layer is substantially free of material covering the central aperture.

According to a sixteenth aspect, the disclosure provides the wound dressing of any of the twelfth through fifteenth aspects, wherein the backing layer is water impermeable and vapor permeable.

According to a seventeenth aspect, the disclosure provides the wound dressing of any of the twelfth through sixteenth aspects, wherein the upper substrate is an absorbent layer.

According to an eighteenth aspect, the disclosure provides the wound dressing of any of the twelfth through seventeenth aspects, wherein the upper substrate is a moisturizing layer.

According to a nineteenth aspect, the disclosure provides the wound dressing of any of the twelfth through eighteenth aspects, the cover layer further comprising a moisture-retentive foam, film, hydrogel, hydrocolloid, biologic, alginate, or combination thereof.

According to a twentieth aspect, the disclosure provides the wound dressing of any of the twelfth through nineteenth aspects, wherein the upper substrate extends between the upper adhesive and the bottom surface of the backing layer.

According to a twenty-first aspect, the disclosure provides a wound dressing as shown and described herein.

According to a twenty-second aspect, the disclosure provides a method for changing a wound dressing as shown and described herein.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A wound dressing comprising:
   a skin contact layer comprising:
      a lower substrate extending around a central aperture, the lower substrate comprising a top surface and a bottom surface opposite the top surface; and
      a lower adhesive disposed on the bottom surface of the lower substrate; and
   a cover layer removably adhered to the top surface of the skin contact layer such that the cover layer can be completely removed from the skin contact layer and, when placed, substantially covers the central aperture of the lower substrate, the cover layer comprising an upper substrate, a backing layer, and an upper adhesive positioned between the top surface of the lower substrate and a bottom surface of the backing layer of the cover layer.

2. The wound dressing of claim 1, wherein a material of the lower substrate of the skin contact layer is fluid-permeable.

3. The wound dressing of claim 1, wherein the lower adhesive comprises skin cement or super glue.

4. The wound dressing of claim 1, wherein the skin contact layer further comprises a porous non-adhesive area covering the central aperture.

5. The wound dressing of claim 1, wherein the skin contact layer is substantially free of material covering the central aperture.

6. The wound dressing of claim 1, wherein the backing layer is water impermeable and vapor permeable.

7. The wound dressing of claim 1, wherein the upper substrate is an absorbent layer.

8. The wound dressing of claim 1, wherein the upper substrate is a moisturizing layer comprising a moisturizing compound.

9. The wound dressing of claim 1, wherein the upper adhesive has an adhesion factor less than an adhesion factor of the lower adhesive.

10. The wound dressing of claim 1, wherein the cover layer further comprises a moisture-retentive foam, film, hydrogel, hydrocolloid, biologic, alginate, or combination thereof.

11. The wound dressing of claim 1, wherein the upper substrate extends between the upper adhesive and the bottom surface of the backing layer.

12. A wound dressing comprising:
    a skin contact layer comprising:
       a lower substrate extending around a central aperture and comprising a top surface and a bottom surface opposite the top surface, wherein the lower substrate is fluid-permeable; and
       a lower adhesive disposed on the bottom surface of the lower substrate; and
    a cover layer removably adhered to the top surface of the skin contact layer such that the cover layer can be completely removed from the skin contact layer and, when placed, substantially covers the central aperture of the lower substrate, the cover layer comprising an upper substrate and a backing layer, wherein an upper adhesive is positioned between the top surface of the lower substrate and a bottom surface of the backing layer and wherein the upper adhesive has an adhesion factor less than an adhesion factor of the lower adhesive.

13. The wound dressing of claim 12, wherein the lower adhesive comprises skin cement or super glue that maintains adhesion for an extended period of time.

14. The wound dressing of claim 12, wherein the skin contact layer further comprises a porous non-adhesive area covering the central aperture.

15. The wound dressing of claim 12, wherein the skin contact layer is substantially free of material covering the central aperture.

16. The wound dressing of claim 12, wherein the backing layer is water impermeable and vapor permeable.

17. The wound dressing of claim 12, wherein the upper substrate is an absorbent layer.

18. The wound dressing of claim 12, wherein the upper substrate is a moisturizing layer comprising a moisturizing compound.

19. The wound dressing of claim 12, wherein the cover layer further comprises a moisture-retentive foam, film, hydrogel, hydrocolloid, biologic, alginate, or combination thereof.

20. The wound dressing of claim 12, wherein the upper substrate extends between the upper adhesive and the bottom surface of the backing layer.

* * * * *